United States Patent [19]
Tanielian et al.

[11] Patent Number: 5,754,044
[45] Date of Patent: May 19, 1998

[54] MAGNETOOPTIC SYSTEM FOR ARTICLE DEFECTS AND FLAWS DETECTION

[76] Inventors: Aram Tanielian, 7013 Cherty Dr., Rancho Palos Verdes, Calif. 90275; George D. Carlsen, II, 1145 Sea Village Dr., Cardiff, Calif. 92007; Alexey L. Solodov, Dibenko Street, 32-2-134, 125475 Moscow, Russian Federation; Andrey Ya Chervonenkis, 113461, Sevastopolsky Prospect, 75-2-86, Moscow, Russian Federation; Vladimir L. Gribkov, Octyabrskaya st. 75-49, 140061 Litkarino, Moscow regeon, Russian Federation; Nikolay N. Kiryuhin, Sholkovskoe shorse, 33-69, 107241 Moscow, Russian Federation

[21] Appl. No.: 349,421

[22] Filed: Dec. 5, 1994

[51] Int. Cl.$^6$ .............. G01R 33/00; G01R 33/12; G01N 27/82
[52] U.S. Cl. .............. 324/263; 324/213; 324/235
[58] Field of Search .............. 324/213, 214, 324/215, 216, 263, 226, 235, 238

[56] References Cited

U.S. PATENT DOCUMENTS

| | | | |
|---|---|---|---|
| 2,764,733 | 9/1956 | De Forest | 324/213 |
| 3,013,206 | 12/1961 | Youngqist et al. | 324/213 |
| 4,755,752 | 7/1988 | Fitzpatrick | 324/213 |

*Primary Examiner*—Walter E. Snow
*Attorney, Agent, or Firm*—Charles C. Logan, II

[57] ABSTRACT

A magnetooptic device to be used in industrial applications to investigate articles for flaws or defects. The magnetooptic device is capable of revealing defects in articles of nonmagnetic and magnetic conducting material. These results are achieved by designing a magnetooptic device having a magnetooptic transformer element on its bottom surface and incorporating a front electrical contact and a rear electrical contact on the bottom surface of the MO device. The respective electrical contacts are connected by wire conductors to the respective positive and negative terminals of a source of electrical current. The defect pattern of an article can be either visually viewed or the defect pattern can be recorded on a tape or magnetic rubber sheet placed between the bottom surface of the MO device and the top surface of the article being analyzed.

12 Claims, 3 Drawing Sheets

MAGNETOOPTIC SYSTEM FOR ARTICLE DEFECTS AND FLAWS DETECTION

BACKGROUND OF THE INVENTION

The invention relates to the field of investigating material flaws and defects with the help of magnetic means. The invention takes the form of a magnetooptic (MO) flaw detector that is used in industrial applications. Its principle is based upon flaw revealing by currents.

Presently there is a known magnetooptic device for article quality control that contains a magnetooptic visualizer of a spatially inhomogeneous magnetic field. The major shortcoming of this device is its inability to reveal defects in articles made of nonmagnetic current conducting materials, because it is intended only for magnetically hard materials.

There is also a prior art magnetooptic visualizer of a spatially inhomogeneous magnetic field having a magnetooptic transformer. This device is also used for article quality control. The shortcomings of this device is its inability to detect flaws in articles of nonmagnetic materials, because it is intended only for magnetically soft materials.

It is an object of the invention to provide a novel magnetooptic device that will reveal the defects in articles formed of nonmagnetic and magnetic conducting materials.

It is also an object of the invention to provide a novel magnetooptic device that is economical to manufacture and market.

It is another object of the invention to provide a novel magnetooptic device that may additionally contain a memory element made of magnetic material.

SUMMARY OF THE INVENTION

The novel magnetooptic device for article quality control has an elongated housing made of plastic or nonmagnetic material. Two spring loaded electrical contacts are mounted in the bottom surface of the housing, with one normally being located adjacent its forward end and the other being located adjacent its rear end. Also mounted on the bottom surface of the housing, intermediate the respective electrical contacts, is a magnetooptic (MO) transformer element that has been processed in such a way that when it is subjected to a magnetic field, it causes a polarization rotation in either one direction or another depending upon the polarity of the magnetic field. An example of such a magnetooptic transformer element would be a uniaxial anisotropical single crystalline of Bi-substituted iron garnet film. This film would have been grown epitaxially on a substrate of gadolinium-gallium garnet.

The top surface of the MO transformer element is intersected by an X axis and a Y axis. The X-axis extends upwardly at an acute angle to the bottom surface of the housing and along this X-axis is an elongated chamber formed in the housing. A light source is positioned adjacent the top end of the chamber and it projects light downwardly through a collimating lens in the chamber. After the light passes through the collimating lens it passes through a film polarizing element as it travels toward the top surface of the MO transformer. The light rays reflect off the MO transformer and are directed upwardly at an acute angle along a Y-axis through an elongated viewing chamber formed in the housing. The reflected light rays first pass through an analyzer in the form of a film polarizing element and then through an optical lens for visual examination. A source of electrical current has its positive terminal connected by a wire connector to one of the electrical contacts of the MO device. The negative terminal of the electrical current source is connected by a wire conductor to the other electrical contact. The source of electrical current can be D.C. or pulse current, as well as A.C. current, where the source of pulse may be fulfilled as a source of bipole or monopole current pulses.

The electrical current conducting contacts may be formed from a rectangular platelet that is formed into a cylindrical surface or it may be flat with spike edges at its ends. The distance between the electrical current conducting contacts may exceed the maximum dimensions of the visualizing area.

The MO device may additionally be used with a memory element, made of magnetic material, which is magnetically connected to the bottom surface of the MO transformer. The memory element may be made of a sheet of magnetic rubber or magnetic tape that is placed on the top surface of the object to be investigated for flaws or defects by the magnetooptic device. The memory element is then connected to the terminals of a source of electrical current. The defect pattern is then recorded on the memory element and it is later analyzed by using the MO device.

In operation the magnetooptic device has its electrical current conducting contacts linked to the article being analyzed for flaws and the current is supplied to the surface of the article between the respective contacts. The current distribution in the article being analyzed is dependent upon whether there is a defect in the zone of control or not. In the presence of a defect the stray field, induced by the current is changed, that is registered by the MO visualizer of magnetically inhomogeneous magnetic field. Hence, by the analysis of spatially inhomogeneous magnetic stray fields, one can judge about the location and nature of the defect. Magnetic stray fields are able to produce an "imprint" on the memory element, made of moderately magnetically hard material (magnetic rubber, magnetic tape), that might be used for documentation of the defects and their further investigation in the laboratory.

A video camera can be connected to the viewing chamber of the MO device and the visualized defect pattern can be recorded on video tape and/or displayed on a CRT screen. In this embodiment the magnetooptic transformer element may be made of a high coercivity magnetooptic film with memory capability. The magnetooptic transformer element may also be made of a low coercivity magnetooptic film with ordered domain structure the change of which has memory capability.

The magnetooptic device can be used with D.C. current, but unfortunately it requires high electrical consumption. For lower power of consumption, either A.C. or pulse current would be used, however it is necessary to take into account the dynamic effects that take place in the MO transformer.

Examining flat articles, the current-conducting contacts may be in the form of a rectangular platelet. For examining tubular surfaces, the contacts may be formed with a cylindrical surface. If the article is covered by paint, contacts with spike like edges would be used.

DESCRIPTION OF THE PREFERRED EMBODIMENT

Figure 1:
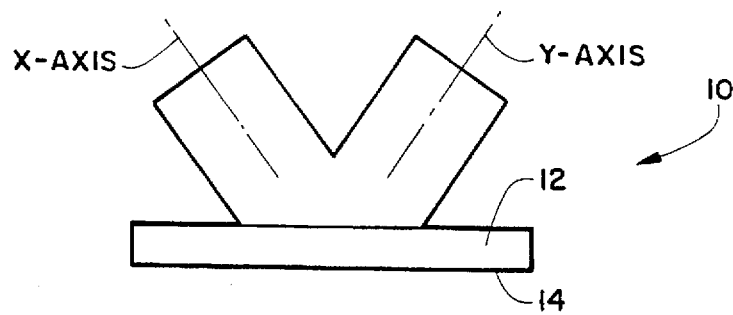
FIG. 1 is a side elevation view of the novel magnetooptic device.
Figure 2:
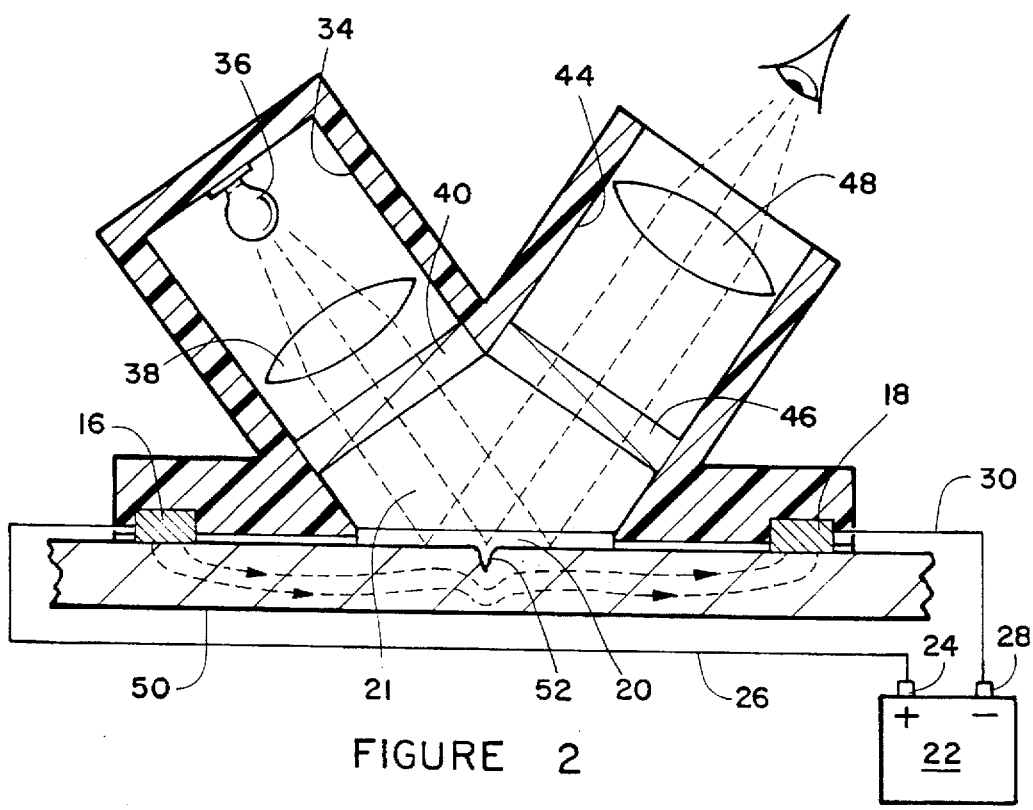
FIG. 2 is a schematic side elevation view of the magnetooptic device showing the manner in which an article is examined for defects and flaws.

The magnetooptic device for article quality control will now be described by referring to FIGS. 1–5 of the drawings. The magnetooptic device is generally designated numeral 10.

Magnetooptic device 10 has a housing 12 having a bottom surface 14. Mounted on bottom surface 14 is a front electrical contact 16 and a rear electrical contact 18. Also positioned on the bottom surface of housing 12 is the MO transformer 20. A source of electrical power 22 has a positive terminal 24 that is connected by wire conductor 26 to front electrical contact 16. Negative terminal 28 is connected by wire conductor 30 to rear electrical contact 18.

Source of electrical power 22 may be D.C. current, A.C. current, or a pulse current. If a pulse current is used, it may be a unipole current pulse or a bi-pole current pulse.

An X-axis and a Y-axis intercept the top surface of Mo transformer 20. A cavity 21 is formed in housing 12 immediately above the top surface of MO transformer element 20. Housing 12 has a light projection chamber 34 extending upwardly along the X-axis from cavity 21 and it has a light source 36 positioned adjacent its top end. Light from source 36 is directed through a collimating lens 38 and a polarizer element 40 prior to reflecting off the top surface of MO transformer 20. Housing 12 also has an upwardly extending viewing chamber 44 that lies along the Y-axis extending upwardly from cavity 21. The light rays reflected from MO transformer 20 pass through an analyzer element 46 and then through an optical lens 48 before being visually viewed. The article 50 that is being analyzed for flaws and defects is shown to have a defect 52. The electrical lines of current passing through article 50 between electrical contact 16 and 18 are caused to deviate their path of travel around defect 52. The MO transformer 20 produces a visualized defect pattern that can be viewed through optical lens 48.

Figure 3:
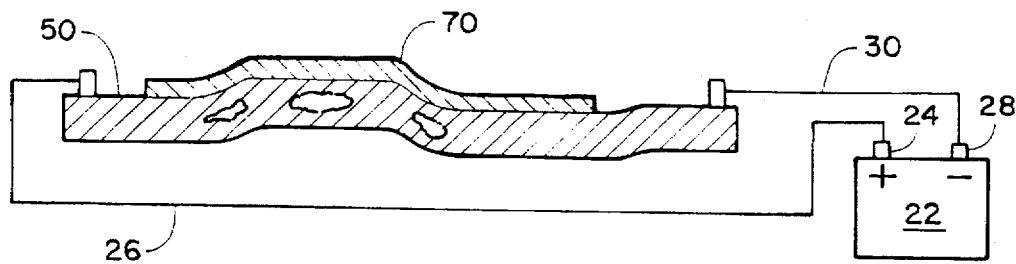
FIG. 3 is a schematic side elevation view showing a tape or magnetic sheet positioned on the top surface of the article to be examined with electric connections.
Figure 4:
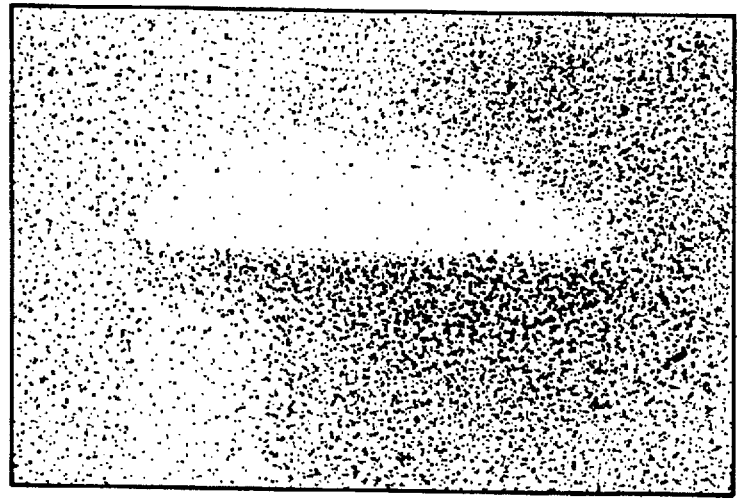
FIG. 4 illustrates a visualized defect pattern.
Figure 5A:
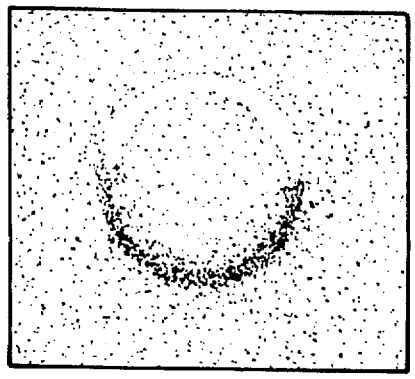
FIGS. 5A and 5B illustrate MO patterns of defects on magnetic tape or a magnetic ribbon sheet that is revealed by electrical current passing through a copper film with a defect.
Figure 5B:
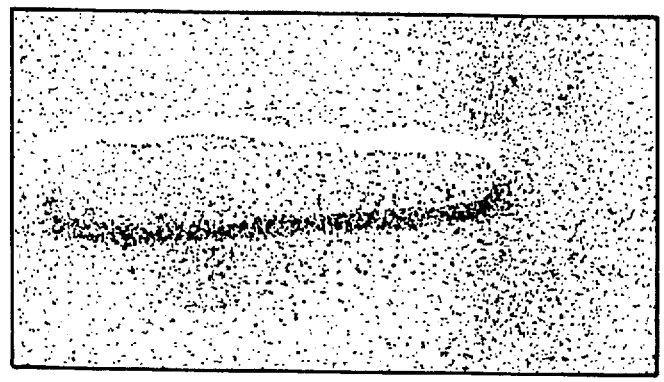
Figure 6:
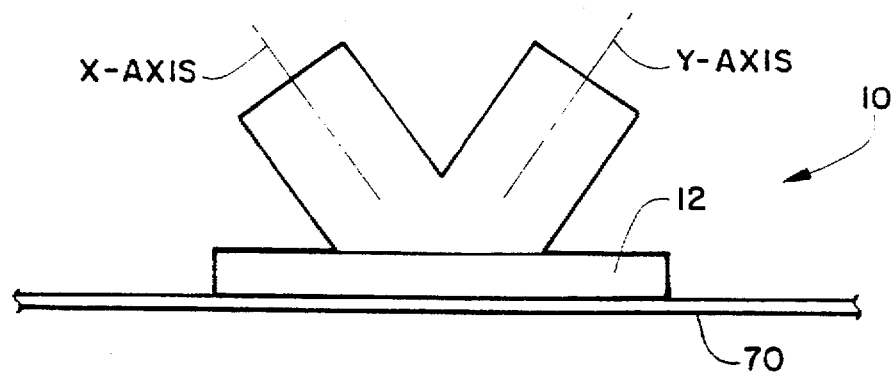
FIG. 6 illustrates novel magnetooptic device positioned on the top surface of the tape or magnetic sheet of FIG. 3.

FIG. 3 is a schematic diagram showing a tape or magnetic rubber sheet 70 positioned upon the top surface of article 50. Current from electrical source 22 allows a visualization of the defect to be recorded. After the visualization of the defect has been recorded on the tape or magnetic rubber sheet 70, the novel magnetooptic device 10 is used to visually inspect the tape or magnetic rubber sheet for defects in article 50 (see FIG. 6). FIG. 4 illustrates a visualized defect pattern. FIGS. 5A and 5B illustrates the defect pattern on magnetic tape or a magnetic rubber sheet.

What is claimed is:

1. A magnetooptic system for detecting flaws in the material of an article comprising:

a magnetooptic flaw detector having a housing of nonmagnetic material having a first end, a second end, a bottom surface and a top surface, a first electrical current conducting contact and a second electrical current conducting contact are spaced from each other by the nonmagnetic material of said housing and are positioned on said bottom surface, a magnetooptic (MO) transformer element having a top surface is positioned on said bottom surface intermediate said first electrical current conducting contact and said second electrical current conducting contact;

a cavity is formed in said housing above the top surface of said MO transformer element, an X-axis extends upwardly from the top surface of said MO transformer element and along this x-axis is formed a light projection chamber in said housing, said light projection chamber having a top end and a light source is positioned adjacent said top end; a film polarizing element is mounted on said X-axis intermediate said light source and the top surface of said MO transformer element; a Y-axis also extends upwardly from the top surface of said MO transformer element and along this axis is formed a viewing chamber in said housing; said viewing chamber having a top end and an optical lens is positioned adjacent said top end; a film polarizing element is mounted on said Y-axis intermediate said optical lens and the top surface of said MO transformer element;

a source of electrical power having a positive terminal and a negative terminal;

means electrically connecting the positive terminal of said electric power source to said first electrical current conducting contact;

means electrically connecting the negative terminal of said electric power source to said second electrical current conducting contact so that electrical current can pass through an article being inspected from said first electrical current conducting contact to said second electrical conducting contact; and a memory element made from magnetic material magnetically connected to the bottom surface of said magnetooptic transformer.

2. A magnetooptic system for detecting flaws in the material of an article comprising:

a magnetooptic flaw detector having a housing of nonmagnetic material having a first end, a second end, a bottom surface and a top surface, a first electrical current conducting contact and a second electrical current conducting contact are spaced from each other by the nonmagnetic material of said housing and are positioned on said bottom surface, a magnetooptic (MO) transformer element having a top surface is positioned on said bottom surface intermediate said first electrical current conducting contact and said second electrical current conducting contact;

a cavity is formed in said housing above the top surface of said MO transformer element, an X-axis extends upwardly from the top surface of said MO transformer element and along this x-axis is formed a light projection chamber in said housing, said light projection chamber having a top end and a light source is positioned adjacent said top end; a film polarizing element is mounted on said X-axis intermediate said light source and the top surface of said MO transformer element; a Y-axis also extends upwardly from the top surface of said MO transformer element and along this axis is formed a viewing chamber in said housing; said x-axis and said y-axis intersect each other at an acute angle; said viewing chamber having a top end and an optical lens is positioned adjacent said top end; a film polarizing element is mounted on said Y-axis intermediate said optical lens and the top surface of said MO transformer element;

a source of electrical power having a positive terminal and a negative terminal;

means electrically connecting the positive terminal of said electric power source to said first electrical current conducting contact; and means electrically connecting the negative terminal of said electric power source to said second electrical current conducting contact so that electrical current can pass through an article being inspected from said first electrical current conducting contact to said second electrical conducting contact.

3. A magnetooptic system for article defects and flaws detection as recited in claim 2 wherein said source of electrical power is direct current (D.C.).

4. A magnetooptic system for article defects and flaws detection as recited in claim 2 wherein said source of electrical power is alternating current (A.C.).

5. A magnetooptic system for article defects and flaws detection as recited in claim 2 wherein said source of electrical power is a pulse current.

6. A magnetooptic system for article defects and flaws detection as recited in claim 5 wherein said pulse current has bipole current pulses.

7. A magnetooptic system for article defects and flaws detection as recited in claim 5 wherein said pulse current has unipole current pulses.

8. A magnetooptic system for article defects and flaws detection as recited in claim 2 wherein said magnetooptic transformer is made of a high coercivity magnetooptic film with memory capability.

9. A magnetooptic system for article defects and flaws detection as recited in claim 2 wherein said magnetooptic transformer is made of a low coercivity magnetooptic film with ordered domain structure the change of which has memory capability.

10. A magnetooptic system for article defects and flaws detection as recited in claim 1 wherein said memory element is made of magnetic rubber.

11. A magnetooptic system for article defects and flaws detection as recited in claim 1 wherein said memory element is made of magnetic tape.

12. A magnetooptic system for article defects and flaws detection as recited in claim 2 wherein the distance between said first and second electrical contacts is greater than dimension of said magnetooptic transformer.

\* \* \* \* \*